United States Patent
Pameijer et al.

(10) Patent No.: US 7,128,573 B2
(45) Date of Patent: Oct. 31, 2006

(54) DEVICE FOR DETERMINING SHADES OF DENTAL RESTORATIONS

(75) Inventors: Cornelis H. Pameijer, Simsbury, CT (US); Weitao Jia, Wallingford, CT (US)

(73) Assignee: Pentron Clinical Technologies, LLC, Wallingford, CT (US)

( * ) Notice: Subject to any disclaimer, the term of this patent is extended or adjusted under 35 U.S.C. 154(b) by 0 days.

(21) Appl. No.: 11/058,534

(22) Filed: Feb. 15, 2005

(65) Prior Publication Data

US 2005/0186527 A1    Aug. 25, 2005

Related U.S. Application Data

(60) Provisional application No. 60/545,843, filed on Feb. 19, 2004.

(51) Int. Cl.
*A61C 19/10* (2006.01)

(52) U.S. Cl. ...................................... 433/26

(58) Field of Classification Search ............ 433/26, 433/34, 141–146, 40, 202.1, 213, 171, 223; 264/19, 20; 425/121; 29/530, 418
See application file for complete search history.

(56) References Cited

U.S. PATENT DOCUMENTS

| | | | |
|---|---|---|---|
| 4,618,325 A | 10/1986 | Appelle | |
| 4,717,341 A | 1/1988 | Goldberg et al. | |
| 4,810,193 A * | 3/1989 | Wieder | 433/26 |
| 4,894,012 A | 1/1990 | Goldberg et al. | |
| 4,919,616 A * | 4/1990 | Croll | 433/26 |
| 5,114,340 A * | 5/1992 | Hahn | 433/26 |
| 5,564,929 A | 10/1996 | Alpert | |
| 5,684,103 A | 11/1997 | Jia et al. | |
| 5,725,372 A | 3/1998 | Leon | |
| 5,919,044 A | 7/1999 | Sicurelli, Jr. et al. | |
| 5,989,022 A | 11/1999 | Yamamoto et al. | |
| 6,013,694 A | 1/2000 | Jia et al. | |
| 6,030,220 A | 2/2000 | Karmaker et al. | |
| 6,039,569 A | 3/2000 | Prasad et al. | |
| 6,417,246 B1 | 7/2002 | Jia et al. | |
| 6,653,365 B1 | 11/2003 | Jia | |
| 6,663,385 B1 * | 12/2003 | Tepper | 433/11 |
| 6,767,955 B1 | 7/2004 | Jia | |
| 6,787,629 B1 | 9/2004 | Jia et al. | |

* cited by examiner

*Primary Examiner*—Todd E. Manahan
*Assistant Examiner*—Meoghan E. MacPherson
(74) *Attorney, Agent, or Firm*—Ann M. Knab

(57) ABSTRACT

A device for verifying the shade of a patient's teeth for the fabrication of a dental restorative comprising a mold section and a section for holding a shade tab, both of which are disposed on the shaft or rod of the device. A shade tab is formed in the mold section by applying composite material in the mold and curing it. The composite material is selected by the dentist based on the shade of the patient's teeth. After the composite material is cured, the resultant shade tab is removed from the mold and placed in the holder for the shade tab. This enables a dentist to effectively match the shade of a patient's teeth in order to provide a restoration that matches the patient's teeth.

25 Claims, 5 Drawing Sheets

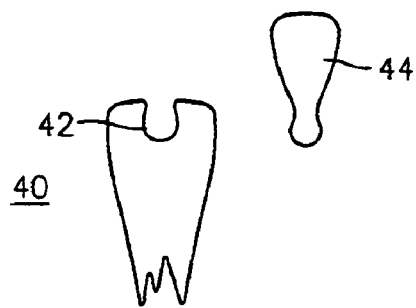
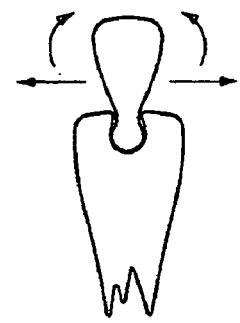
FIG. 5        FIG. 6
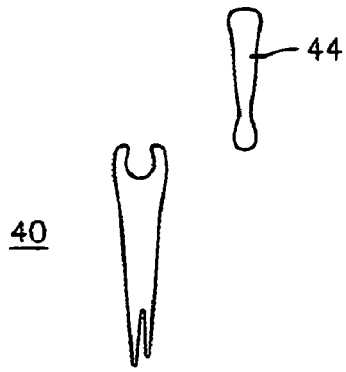
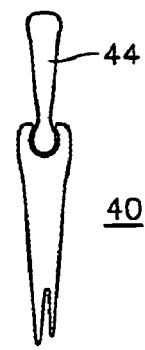
FIG. 7        FIG. 8

DEVICE FOR DETERMINING SHADES OF DENTAL RESTORATIONS

CROSS-REFERENCE TO RELATED APPLICATIONS

This application claims the benefit of U.S. Provisional Patent Application Ser. No. 60/545,843 filed Feb. 19, 2004.

FIELD OF THE INVENTION

The present invention relates to a device and method for determining the shades of dental restorations.

BACKGROUND OF THE INVENTION

Over the years, dentists have had the ability to restore the exposed surfaces of patients'teeth with material which quite accurately duplicates each patient's tooth anatomy so as to present a repair or restoration which visually blends with the rest of the patient's natural teeth. The restorative material is generally a photocurable or hardenable resin or composite material.

The uncured resin or paste material, once selected, is applied to a patient's tooth surface and an appropriate light source is directed at the surface to cure and harden the material in a very short time period.

One of the major drawbacks to such repair resides in the accurate selection of the color or shade of the restorative material. A number of suppliers provide restorative materials in a broad variety of shades for selection by the dentist. Accompanying each restorative material kit is typically a color sample which includes a plurality of plastic pieces each having a shape similar to a human tooth and each having a different shade which is intended to represent the color of each particular material by code or name designation.

In practice, however, the majority, if not all of the associated samples provided by the manufacturers of each restorative material do not accurately reflect the true shade of the material which correlates with the sample provided. Further, in most, if not all cases, the shade samples provided by the manufacturers are fabricated or molded of a plastic material which is not identical in content or in consistency to the restorative material itself.

Furthermore, the shade samples offered by manufacturers are designed to be used for the lifetime of the material system and are subject to repeated use by a dentist. The samples are required to be sanitized between usage, which can be quite burdensome.

In any event, the dentist utilizing the restorative material is at a serious disadvantage when attempting to select a restorative material which identically matches a particular patient's tooth or teeth to be repaired. The dentist must compare the samples provided with the coloration of the patient's teeth and then make the selection accordingly. However, many times there are inconsistencies in the coloration of the samples provided and the actual restorative material. As a result, the finished dental product typically does not identically match the rest of the patient's original teeth.

It is therefore desirable to provide a method whereby a dentist can easily match the shade of the dental restorative material to the patient's teeth. It is further desirable to provide disposable shade verifying devices. It would be beneficial to provide shade tabs that accurately match the shade of a patient's teeth.

SUMMARY OF THE INVENTION

These and other objects and advantages are accomplished by the shade verifying device of the present invention comprising a mold section and a section for holding a shade tab, both of which are disposed on the shaft or rod of the device. A shade tab is formed in the mold section by applying composite or similar material in the mold and curing it. The composite material is selected by the dentist based on the perceived shade of the patient's teeth. After the composite material is cured, the resultant shade tab is removed from the mold and placed in the shade tab holder for the shade tab. This enables a dentist to comparatively match the shade of a patient's teeth in order to provide a restoration that matches the patient's teeth.

BRIEF DESCRIPTION OF THE DRAWINGS

Features of the present invention are disclosed in the accompanying drawings, wherein similar reference characters denote similar elements throughout the several views, and wherein:

FIG. 5 is a cut-away front view of a shade tab device and shade tab;

FIG. 6 is a cut-away front view of the shade tab device of FIG. 5 with the shade tab positioned therein;

FIG. 7 is a cut-away side view of FIG. 5;

FIG. 8 is a cut-away side view of FIG. 6;

DESCRIPTION OF THE INVENTION

Figure 1:
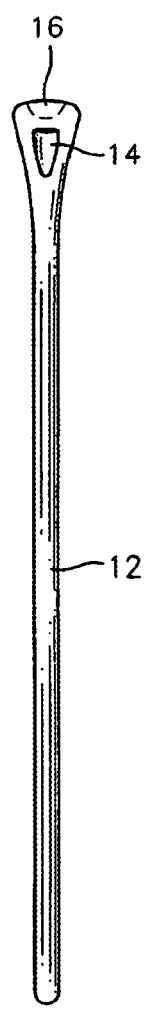
FIG. 1 is a front perspective view of a shade tab device in accordance with the invention.
Figure 2:
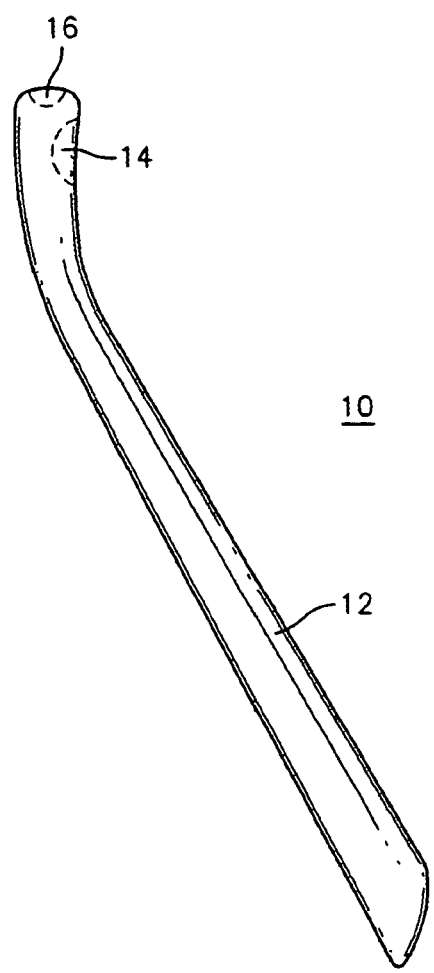
FIG. 2 is a side view of the shade tab device in FIG. 1.

As will be appreciated, the present invention provides a device for effectively and accurately determining the color of a restoration. Attention is directed to FIGS. 1 and 2, which show a shade tab device 10 having a rod or shaft 12. A mold section 14 is positioned on rod 12 proximate the top end of rod 12. Although mold section 14 is shown positioned proximate the top end of rod 12, it may be positioned anywhere along the length of rod 12. Moreover, rod 12 may include more than one mold section. The mold sections may be of different shapes and thicknesses. This can enable the practitioner to see how thickness of a sample affects the shade of the restoration.

Figure 3:
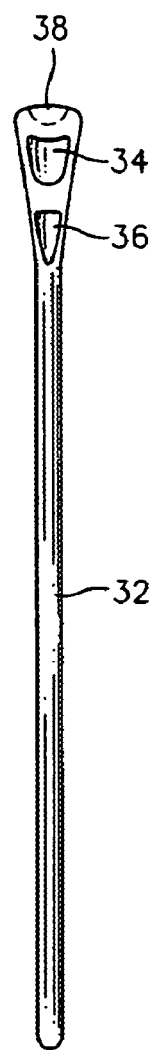
FIG. 3 is a front perspective view of an alternate embodiment of a shade tab device in accordance with the invention.
Figure 4:
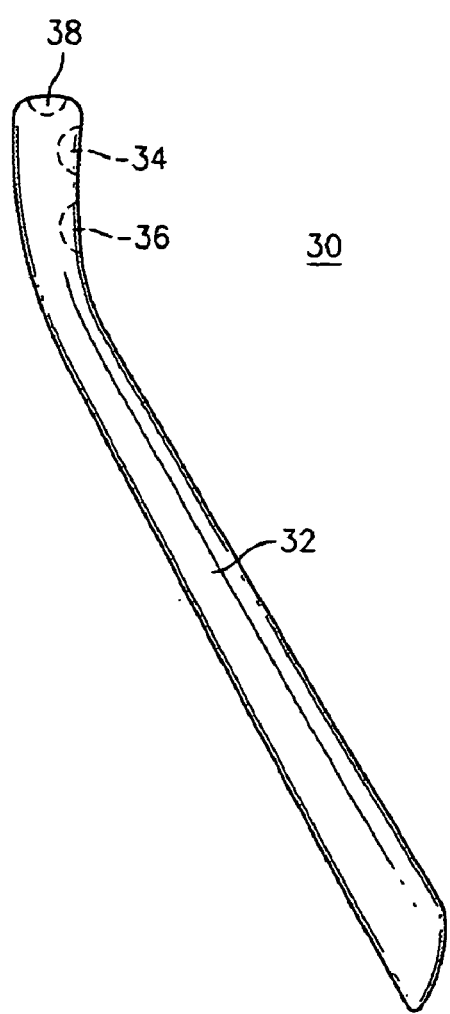
FIG. 4 is a side view of the shade tab device in FIG. 3.

FIGS. 3 and 4 show a shade tab device 30 having a rod 32 having two mold sections 34 and 36 disposed near the top end of rod 32. Mold section 34 is in the shape of a posterior tooth while mold section 36 is in the shape of an anterior tooth. The mold sections may be of any shape desirable including, but not limited to, concave grooves in the shape of an oval, a circle, a square, or a rectangle, a tapered or graduated wedge, or in the shape of a tooth, as stated above.

The shade tab devices 10 and 30, each include a shade tab holder 16 and 38, respectively. Shade tab holders 16 and 38 are shown positioned on the top end of devices 10 and 30, respectively. The position of the shade tab holder is not limited to the positions shown and it may be positioned in a place along the length of or at either end of the device as long as the position allows ease of use for the dental practitioner when comparing the shade of the tab to the shade of a tooth or teeth in a patient's mouth.

The mold section may be shaped such that a tab produced therefrom includes a spherically-shaped or semi-spherically-shaped element which fits or snaps into the tab holder, such that the tab holder acts like a socket. A "ball and socket" connection is created with the shade tab and the cavity or shade tab holder. In this way, the shade tab may be rotated within the shade tab holder for better effect and visibility of the shade when comparing the shade tab to the patient's teeth. FIGS. 5 through 8 show a shade tab device 40 having a groove or notch 42 shaped spherically. Shade tab 44 may be inserted into device 40 as shown in FIG. 6 and may be rotated in any direction as indicated in the drawing. FIGS. 7 and 8 show shade tab device 40 and shade tab 44 as viewed from the side.

Figure 9:
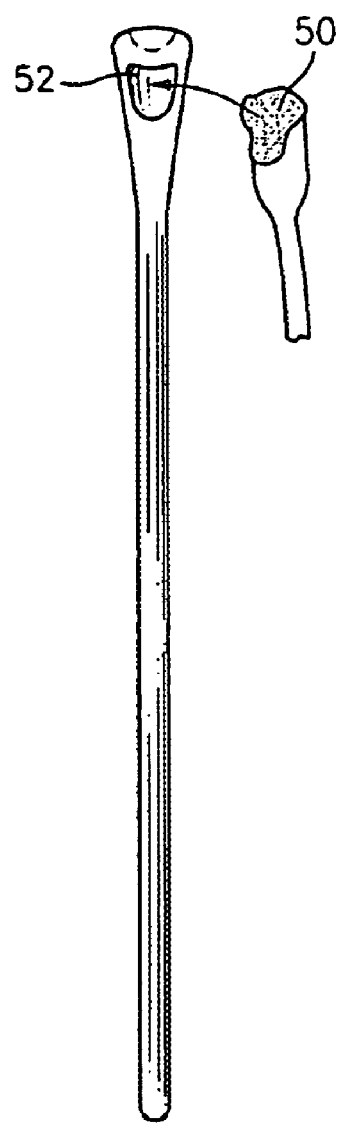
FIG. 9 is a front perspective view of a shade tab device in accordance with the invention showing the placement of uncured dental material therein.
Figure 10:
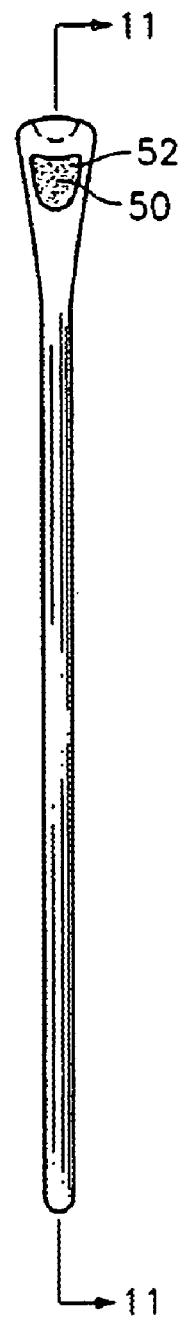
FIG. 10 is a front perspective view of the shade tab device of FIG. 9 with the dental material placed therein.
Figure 11:
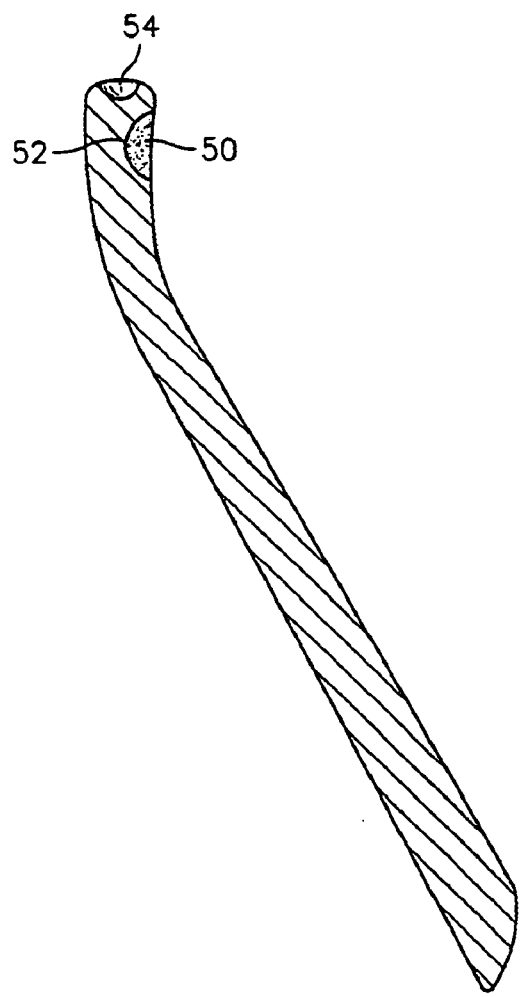
FIG. 11 is a sectional side view of FIG. 10 along line 11—11.

Referring to FIGS. 9 through 12, the shade tab device is shown in use. In FIG. 9, an uncured dental restorative paste 50 is ready for placement in mold section 52. FIGS. 10 and 11 depict paste 50 positioned in mold section 52. The shade tab may be fabricated of light, heat, pressure and/or self curable restorative materials, such as resinous and polymeric materials including, but not limited to, fiber-reinforced composite materials, filler-reinforced composite materials and combinations thereof. Examples of materials are also set forth in commonly owned U.S. Pat. Nos. 6,787,629, 6,767,955, 6,653,365, 6,417,246, 6,013694, and 5,684,103, all of which are hereby incorporated by reference. Commercially available materials useful herein include, but are not limited to, ALERT® composite, SIMILE® composite, FLOW-IT® composite and SCULPTURE-PLUS™ composite, all available from Pentron Clinical Technologies, LLC, Wallingford, Conn.

Figure 12:
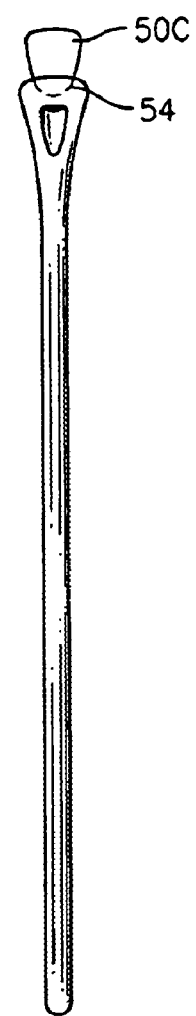
FIG. 12 is a front perspective view of the shade tab device in accordance with the invention showing a cured dental material shade tab therein.

After placement in mold section 52, the restorative paste 50 is cured using known curing techniques to provide a shade tab 50C (cured dental restorative paste). The shade tab 50C is removed from mold section 52 and placed in shade tab holder 54 as shown in FIG. 12. The dentist may now check the shade tab fabricated of dental restorative material with the teeth in a patient's mouth.

It is preferable that the shade tab is removably inserted into the shade tab holder and securely maintained in the tab holder during use of the device. It is further preferable that the shade tab is inserted in the shade tab holder and securely maintained in the tab holder in a snap fit relation so that it can be easily snapped into the holder, maintained therein and easily removed after use.

The shade tab device may be manufactured of any material able to withstand curing procedures for dental restorative materials. Examples of materials useful herein include, but are not limited to, metal, plastic, ceramic, polymeric and composite materials.

Composite materials include but are not limited to filler reinforced composite materials and fiber reinforced composite materials comprising the reinforcing component in a polymeric matrix material such as those composite materials listed in U.S. Pat. Nos. 4,717,341 and 4,894,012 to Goldberg et al., U.S. Pat. No. 6,039,569 to Prasad et al., U.S. Pat. No. 6,030,220 to Karmaker et al, U.S. Pat. No. 5,564,929 to Alpert, and U.S. Pat. No. 5,919,044 to Sicurelli, Jr. et al., all of which are hereby incorporated by reference.

The device herein allows a dentist to quickly and easily fabricate a small tab of restorative material to check the shade of the material to the shade of a patient's teeth. It ensures accurate color matching of the final restoration to the patient's tooth or teeth. The device may be sanitized or autoclaved for further use or it can be disposable.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A device for checking the color of a restoration with a patient's teeth comprising:
   a rod having a first end and a second end;
   at least one mold section disposed on the rod for forming a shade tab; and
   at least one slot disposed on the rod for holding the shade tab; wherein the slot for holding the shade tab comprises a snap fit holder to hold a shade tab in a snap fit connection.

2. The device of claim 1 wherein the first or second end comprises a handle.

3. The device of claim 1 wherein the mold section comprises a concave groove in a shape selected from the group consisting of an oval, a circle, a square, and a rectangle.

4. The device of claim 1 wherein the mold section comprises a concave groove in the shape of a tapered or graduated wedge.

5. The device of claim 1 wherein the mold section comprises a concave groove in the shape of a tooth.

6. The device of claim 5 wherein the shape of the tooth comprises a shape selected from the group consisting of an anterior tooth and a posterior tooth.

7. The device of claim 1 wherein the mold section comprises a shape that forms a spherically-shaped or semi-spherically-shaped section on the shade tab to be molded.

8. The device of claim 7 wherein the slot for holding the shade tab comprises a socket for holding the spherically-shaped or semi-spherically-shaped section so that the shade tab may be rotated in the slot for holding the shade tab.

9. The device of claim 1 wherein the slot is positioned on the top of the first end.

10. The device of claim 1 wherein the mold section is positioned on the periphery of the rod proximate the top of the first end.

11. The device of claim 1 wherein the mold section is positioned anywhere along the length of the rod.

12. The device of claim 1 wherein the rod is slightly curved.

13. The device of claim 1 comprising more than one mold section.

14. The device of claim 13 wherein the mold section comprise different shapes.

15. The device of claim 14 wherein the different shapes comprise an anterior tooth shape and a posterior tooth shape.

16. The device of claim 1 wherein the rod is fabricated of a metal, plastic, ceramic, polymeric, or composite material.

17. The device of claim 16 wherein the composite material comprises fiber-reinforced composite material, filler-reinforced material or a combination thereof.

18. The device of claim 1 wherein the shade tab is manufactured of a dental restorative material.

19. The device of claim 1 wherein the shade tab is manufactured of a heat-curable material, light curable material, pressure curable material, self-curable material or a mixture thereof.

20. The device of claim 1 wherein the shade tab is manufactured of a plastic, polymeric, or composite material.

21. The device of claim 20 wherein the composite material comprises fiber-reinforced composite material, filler-reinforced composite material or a mixture thereof.

22. A method of determining the shade of a restoration for a patient's teeth comprising:
    selecting a shade of dental restorative material that closely matches a patient's teeth;
    providing a device for checking the color of a restoration comprising a rod having a first end and a second end, at least one mold section for forming a shade tab disposed on the rod, and at least one slot for holding the shade tab disposed on the rod;
    applying a small amount of the selected dental restorative material in the mold section of the device;
    curing the selected dental restorative material to form a shade tab;
    removing the shade tab from the mold section and inserting the shade tab into the slot on the device;
    checking the shade tab with the shade of the patient's teeth.

23. The method of claim 22 wherein the shade tab is maintained in the slot in a snap-fit connection.

24. The method of claim 22 wherein the mold section comprises a shape that forms a spherically-shaped or semi-spherically-shaped section on the shade tab to be molded and wherein the slot for holding the shade tab comprises a socket for holding the spherically-shaped section or semi-spherically-shaped so that the shade tab may be rotated in the slot for holding the shade tab.

25. The method of claim 22 wherein the shade tab is rotated in the shade tab slot during the step of checking the shade tab with the shade of the patient's teeth.

* * * * *